United States Patent
Griessmann et al.

(10) Patent No.: US 12,053,566 B2
(45) Date of Patent: Aug. 6, 2024

(54) DIALYSIS MACHINE FOR PERITONEAL DIALYSIS

(71) Applicant: FRESENIUS MEDICAL CARE DEUTSCHLAND GMBH, Bad Homburg (DE)

(72) Inventors: Erik Griessmann, Schweinfurt (DE); Bettina Rathke-Schlaefer, Usingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 644 days.

(21) Appl. No.: 17/287,122

(22) PCT Filed: Oct. 22, 2019

(86) PCT No.: PCT/EP2019/078662
§ 371 (c)(1),
(2) Date: Apr. 21, 2021

(87) PCT Pub. No.: WO2020/083877
PCT Pub. Date: Apr. 30, 2020

(65) Prior Publication Data
US 2021/0386922 A1    Dec. 16, 2021

(30) Foreign Application Priority Data
Oct. 26, 2018  (DE) .................... 10 2018 126 817.3

(51) Int. Cl.
*A61M 1/28*       (2006.01)

(52) U.S. Cl.
CPC .............. *A61M 1/282* (2014.02); *A61M 1/28* (2013.01); *A61M 1/285* (2013.01); *A61M 1/287* (2013.01)

(58) Field of Classification Search
CPC ........ A61M 1/28; A61M 1/282; A61M 1/285; A61M 1/287
See application file for complete search history.

(56) References Cited

U.S. PATENT DOCUMENTS

| | | | |
|---|---|---|---|
| 4,586,920 | A | 5/1986 | Peabody |
| 6,558,343 | B1 | 5/2003 | Neftel |

(Continued)

FOREIGN PATENT DOCUMENTS

| | | |
|---|---|---|
| CN | 1859936 A | 11/2006 |
| CN | 103648539 A | 3/2014 |

(Continued)

OTHER PUBLICATIONS

International Search Report and Written Opinion issued in corresponding International Patent Application No. PCT/EP2019/078662 (with English translation of International Search Report) dated Jan. 30, 2020 (8 pages).

(Continued)

*Primary Examiner* — John Kim
(74) *Attorney, Agent, or Firm* — Kilyk & Bowersox, P.L.L.C.

(57) ABSTRACT

The invention relates to an apparatus for carrying out a peritoneal dialysis treatment comprising a reservoir for fresh dialysis fluid, a connector for connecting to a peritoneal catheter of a patient, a drain for consumed dialysis fluid, and a control unit connected to actuators, wherein the apparatus is configured to carry out a plurality of consecutive inflow-dwell-outflow cycles for a treatment on the basis of a prescription stored in the control unit, in which inflow-dwell-outflow cycles dialysis fluid is supplied to the patient from the reservoir and is led off through the outflow again after the elapse of a specific dwell time in the peritoneum of the patient, and wherein the apparatus is further configured to already replace a portion of the dialysis fluid present in the (Continued)

peritoneum of the patient with fresh dialysis fluid from the reservoir before the elapse of the dwell time in at least one cycle if, in at least one preceding cycle, the volume of fresh dialysis fluid provided in accordance with the prescription for this preceding cycle was not completely consumed.

16 Claims, 8 Drawing Sheets

(56) References Cited

U.S. PATENT DOCUMENTS

| | | |
|---|---|---|
| 2010/0137782 A1 | 6/2010 | Jansson et al. |
| 2010/0191181 A1 | 7/2010 | Childers et al. |
| 2012/0071815 A1 | 3/2012 | Childers et al. |
| 2013/0006171 A1 | 1/2013 | Griessmann et al. |
| 2016/0082173 A1 | 3/2016 | Coll et al. |
| 2017/0157310 A1 | 6/2017 | Scarpaci et al. |
| 2017/0232176 A1 | 8/2017 | Hochrein et al. |
| 2017/0274130 A1 | 9/2017 | Wolf et al. |

FOREIGN PATENT DOCUMENTS

| | | |
|---|---|---|
| DE | 102011105916 A1 | 1/2013 |
| EP | 0498382 B1 | 11/1996 |

OTHER PUBLICATIONS

Search Report issued in corresponding German Patent Application No. 10 2018 126 817.3 dated Jun. 6, 2019 (5 pages).

Office Action issued in corresponding Chinese Patent Application 201980070508.X dated Sep. 29, 2023 (with English translation)(19 pages).

Office Action dated Apr. 16, 2024, from the CNIPA, for corresponding application No. 201980070508.X, with translation (14 pages).

DIALYSIS MACHINE FOR PERITONEAL DIALYSIS

This application is a National Stage Application of PCT/EP2019/078662, filed Oct. 22, 2019, which claims priority to German Patent Application No. 10 2018 126 817.3, filed Oct. 26, 2018.

The invention relates to a dialysis machine for carrying out an automated peritoneal dialysis (APD) treatment.

It is known from WO 2013/000569 A1 in the carrying out of automated peritoneal dialysis treatments to optimize the treatment while observing predefined tolerances and a time aspect as well as under the aspect of the administered volume of dialysis fluid. The definitions of a permitted shortening of the dwell time, of a permitted reduction of the inflow volume, of a permitted residual volume, and of a permitted patient volume are of major importance within the framework of this concept.

The potential use or administration of unused dialysis solution is not considered. If fresh dialysis fluid is still available at the end of the treatment, it is conveyed into the drain on the emptying of the solution bag. However, it frequently occurs in practice that the prescribed total inflow volume of a treatment cannot be fully administered to the patient. The reason for this can in particular be found in the different value ranges for the permitted residual volume and for the permitted patient volume. The permitted residual volume is typically set relatively high in relation to the permitted patient volume so that the patient is not disturbed by outflow failure reports while asleep.

These circumstances are schematically explained in FIG. 1. The permitted patient volume in the example shown there amounts to 120% while the permitted residual volume is fixed at 50%. The prescribed total inflow volume amounts to 5000 ml (5 cycles of 1000 ml). However, only 4,700 ml of solution can be administered due to the automatic switchover in the residual range. Whereas namely a switch to the next inflow can already be made on a reaching of 50% of the outflow volume, only a further 20% of inflow volume can be administered due to the upper limit for the permitted inflow volume. Dialysis solution thus remains unused, which can result in inadequate treatment results, on the one hand, and is also not economical, on the other hand.

To avoid a discarding of the residual fluid, that is, of the difference from the connected dialyzate volume and the actually required volume for the treatment, the prescription of a tidal treatment would be conceivable, with a tidal outflow being administered in a volume controlled manner. The loss of dialysis solution due to the predefined permitted residual volume can thereby be avoided. Since the patient can, however, not be drained as much as by a pressure-controlled outflow in accordance with the standard treatment, the efficiency of the treatment is minimized. The tidal treatment is therefore frequently not prescribed for therapeutic reasons, but only to minimize disturbances and the loss of dialysis fluid. The method described in WO 2010/088360 A1 is to be named in this connection, wherein the remaining treatment is replaced with a tidal treatment in the case of a recognition of an incomplete outflow to convert the administered total volume to achieve a target UF rate. The administered residual inflow volume is here uniformly distributed over the tidal cycles such that the total treatment time is observed.

It would furthermore be conceivable to edit the prescription during the treatment. If a switchover is frequently made at the limit of the permitted residual volume in the course of the treatment to initiate the next inflow phase, there would be a possibility that the user increases the following volumes of the inflows with an editor. The possibility of editing is, however, linked to user rights; the user would have to set an alarm at night and the adaptation is relatively complex.

It would furthermore be conceivable to lower the limit for the permitted residual volume. This can, however, have the result that the patient is woken up more frequently due to disturbances during the treatment. The parameter value for the permitted residual volume is as a rule set high for just this reason to avoid this.

Due to the named disadvantages, however, none of these concepts results in a really satisfactory concept. In addition, the implementation of these concepts is problematic in machines that model the profiled prescriptions, wherein an individual volume of individually adapted dialysis solution can be administered to the patient in each cycle, as shown schematically in FIG. 2.

It is the object of the invention to provide an improved concept for using the residual fluid.

Against this background, the invention relates to an apparatus for carrying out a peritoneal dialysis treatment comprising a reservoir for fresh dialysis fluid, a connector for connecting to a peritoneal catheter of a patient, a drain for consumed dialysis fluid, and a control unit connected to actuators, wherein the apparatus is configured to carry out a plurality of consecutive inflow-dwell-outflow cycles on the basis of a prescription stored in the control unit, in which inflow-dwell-outflow cycles dialysis fluid is supplied to the patient from the reservoir and is led off through the outflow again after the elapse of a specific dwell time in the peritoneum of the patient, and wherein the apparatus is further configured to already replace a portion of the dialysis fluid present in the peritoneum of the patient with fresh dialysis fluid from the reservoir before the elapse of the dwell time in at least one cycle if, in at least one preceding cycle, the volume of fresh dialysis fluid provided in accordance with the prescription for this preceding cycle was not completely consumed.

Provision is therefore made in accordance with the invention to use fresh dialysis solution probably no longer used in accordance with the prescription for a refreshing of the dialysis solution present in the peritoneum of the patient during the dwell phase.

As part of the premature partial replacement, a maximum of 50%, preferably a maximum of 30%, and further preferably a maximum of 20%, of the total volume of dialysis solution present in the peritoneum can be replaced in an embodiment. Within the framework of the invention, it is therefore not a question of the actual integration of further complete drainage and inflow phases, but rather a question of the replacement of only a smaller partial volume of the dialysis fluid present in the peritoneum in order to refresh it.

The dwell time, that is, the duration of the dwell phase of the respective cycle, is preferably not extended or shortened by the premature partial replacement. The dwell time therefore remains constant. If dwell time is spoken of in this connection, the dwell time including the partial replacement procedure is meant. The total treatment time thus remains unchanged.

In this embodiment, the total volume of dialysis fluid present in the peritoneum of the patient is not changed by the premature partial replacement. Provision is therefore made that the total volume of dialysis fluid present in the peritoneum of the patient after the partial replacement procedure corresponds to the total volume of dialysis fluid present in the peritoneum of the patient before the partial replacement procedure. Small deviations occur during the partial replacement procedure.

Provision can alternatively also be made that the volume changes slightly, for example in particular when the partial replacement procedure starts with the inflow step of fresh dialysis solution.

The partial replacement procedure can start both with an inflow step and with a removal step, with the start with the removal step in particular being preferable when the total volume present in the peritoneum of the patient is close to a fixed maximum volume. On the other hand, possible removal problems can be reduced on a start with an inflow step since the removal pressure would then be higher.

The premature partial replacement preferably takes place in inflow and removal steps preferably directly after one another. Due to the division of the removal and inflow of dialysis fluid required for the partial replacement into a plurality of steps, the total volume of the fluid in the peritoneum can be kept approximately constant. A plurality of smaller partial replacement volumes also minimize the risk of outflow problems. If nevertheless a problematic outflow or inflow event occurs, the partial replacement process can be aborted and optionally continued at a later point in time. Alternatively, on the occurrence of an outflow problem, an attempt can be made to continue the partial replacement cycle with an inflow to be able to flush a possibly blocked catheter free.

In this connection, three or more, five or more or the like numbers of inflow steps can be provided, for example, and/or a maximum of 200 ml can be supplied with each inflow step. The effective partial replacement volume can be increased by a high number of small-volume inflow and removal steps during the partial replacement procedure.

Provision is preferably made that the premature replacement is only carried out after the elapse of at least 50% of the provided dwell time and/or that the premature replacement is ended before the elapse of a maximum of 80% of the provided dwell time. After the elapse of half the dwell time, the dialysis fluid present in the peritoneum is as a rule no longer as effective as at the start of the dwell time so that a noticeable increase in efficiency can be achieved by the partial replacement. Too late a replacement only has small effects on the quality of the treatment since the refreshed solution can then no longer develop its effect to a noticeable extent.

In an embodiment, the apparatus is configured to already replace a portion of the dialysis fluid present in the peritoneum of the patient in a plurality of cycles over the course of the treatment with fresh dialysis fluid from the reservoir before the elapse of the dwell time. This has efficiency reasons, on the one hand; on the other hand, the situation with respect to the existing residual volume can, however, also change in the course of the treatment. Dialysis solution thus may have to be discarded, for example, if problems occur or if pumps are repositioned.

In an embodiment, the apparatus is configured only to start a partial replacement cycle when the dwell time provided for the respective cycle in accordance with the prescription exceeds a minimum time. It may not make any sense to generate a partial replacement cycle for cycles having short dwell times due to the short residence time. Suitable minimum times can be fixed, for example, at 45 minutes or 60 minutes.

The determination whether a partial replacement takes place is typically made by the apparatus at the start of a dwell phase since the available and required inflow volume can be determined at this point in time. The dwell time can furthermore be modified. The specified dwell time can, for example, be shortened. One or more outflows and inflows are subsequently administered with small volumes. A further concluding dwell phase follows after the partial replacement. The planned point in time for the subsequent outflow should still be observed so that a treatment extension does not occur.

It could generally also be considered within the framework of the partial replacement, in dependence on availability, to administer a solution having a different glucose concentration than was originally planned for the cycle since the total concentration would only change slightly due to the relatively small amounts.

It is conceivable as an additional effect that an additional positive effect is achieved in treatment efficiency due to the fact that the dialysis solution is circulated by the partial replacement in the peritoneum.

The supply and removal rates during the partial replacement cycle can generally be fixed in accordance with the rates for the inflow and outflow of the cycle or can be smaller or larger. In this connection, very small flow rates can also be provided to carry out a more or less continuous partial replacement.

Optionally, certain minimal volumes that apply to a prescription will not have to be observed for the selection of the partial replacement volume since the partial replacement is not a prescription parameter. A corresponding patient parameter would rather apply overall to all prescriptions.

The invention further relates to an apparatus for carrying out a peritoneal dialysis treatment comprising a reservoir for fresh dialysis fluid, a connector for connecting to a peritoneal catheter of a patient, a drain for consumed dialysis fluid, and a control unit connected to actuators, wherein the apparatus is configured to carry out a plurality of consecutive cycles, typically inflow-dwell-outflow cycles, for a treatment on the basis of a prescription stored in the control unit, in which inflow-dwell-outflow cycles dialysis fluid is supplied to the patient from the reservoir and is led off through the drain again after the elapse of a specific dwell time in the peritoneum of the patient, and wherein the apparatus is further configured to increase the total inflow volume in at least one cycle if, in at least one preceding cycle, the volume of fresh dialysis fluid provided in accordance with the prescription for this preceding cycle was not completely consumed.

Provision is therefore made in accordance with this variant of the invention to use fresh dialysis solution probably no longer required in accordance with the prescription for a augmenting of a later cycle. This variant of the process management could be advantageous for adapted prescriptions since cycles having small and large inflow volumes alternate in this treatment form. The cycles with the small inflow volumes could be raised by, for example, 10% within predefined limits.

The two variants of the process management in accordance with the invention can be combined.

Provision can generally be made that a maximum volume of dialysis fluid that may be present in the peritoneum of the patient is fixed in the control unit and that the incomplete consumption of the volume of fresh dialysis solution provided for the preceding cycle results from the fact that the complete consumption would have led to an exceeding of the maximum volume. The fixing of the maximum volume serves patient safety. The prescription is generally naturally adapted such that the maximum volume is not exceeded, with it, however, not always being able to be considered to a sufficient degree that the peritoneum was only incompletely emptied as part of the preceding drainage phase and the inflow volume fixed in the prescription adds up with the not foreseeable residual volume to form a total volume that can then potentially be above the maximum volume. The residual volume results from the fact that the removal cannot always take place under ideal conditions, in particular during sleep, but that a certain residual volume is tolerated so that the patient is not disturbed by outflow failure reports while asleep.

In an embodiment, the apparatus is configured to supply the patient with the total volume of dialysis fluid provided in accordance with the prescription in the course of the treatment, with any difference quantity that is not supplied as part of the regular inflow phases in particular being completely supplied, in particular on the basis of a consideration of the maximum volume, as part of the premature replacement during the at least one or more cycles. The dialysis solution present or determined for administration in accordance with the prescription is thus sensibly used overall, which is desirable both from a medical and an economic viewpoint.

BRIEF DESCRIPTION OF THE DRAWINGS

Further details and advantages of the invention result from the experiments and embodiments described in the following with reference to the Figures. There are shown in the Figures.

Figure 1:
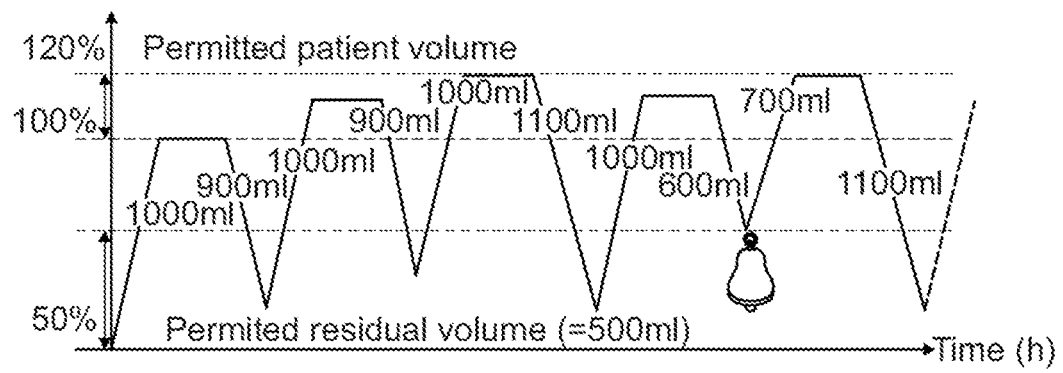
FIG. 1: a schematic representation of a process of an automated peritoneal dialysis treatment, wherein the permitted residual volume is set relatively high in relation to the permitted patient volume and the dialysis solution is therefore not completely consumed.
Figure 2:
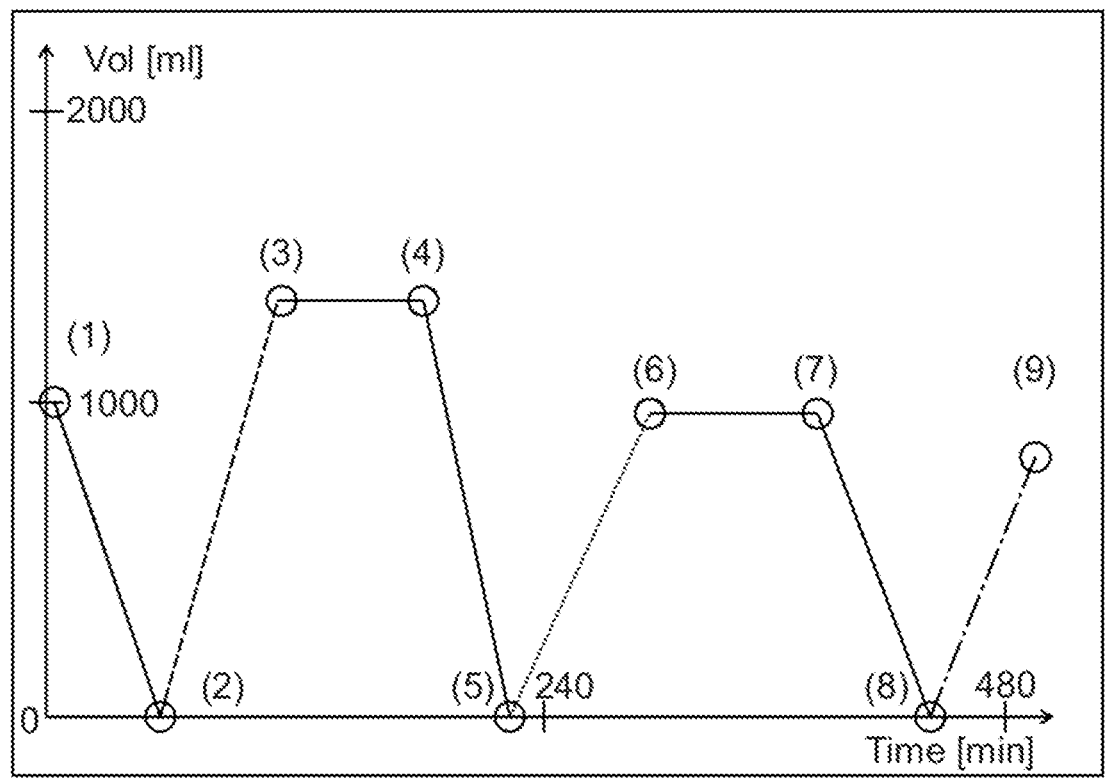
FIG. 2: a schematic representation of a process of an automated peritoneal dialysis treatment with a profiled prescription, wherein solution A is prescribed for inflow 1, solution B for inflow 2, and solution C for the last inflow (profiled solutions), and wherein the inflow volumes and the dwell times for the two cycles also vary (profiled volumes and profiled dwell times)
Figure 3:
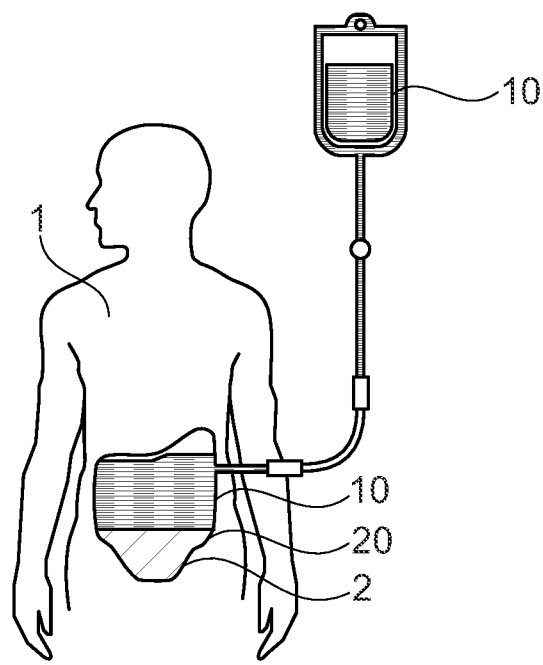
FIG. 3: a schematic representation of the convergence of residual solution present in the peritoneum of the patient and fresh solution during the inflow.
Figure 4:
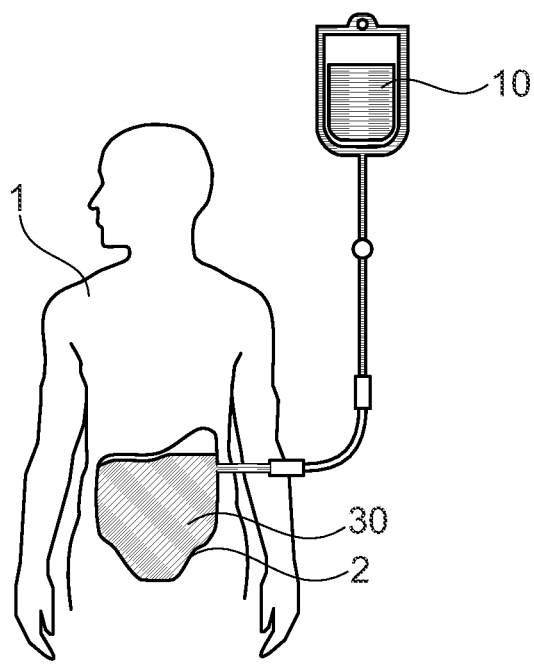
FIG. 4: a schematic representation of the mixing of the residual solution and the fresh solution.

The advantages of the invention can best be explained with reference to the following considerations. As can be recognized from FIG. 3, a present residual solution 20 and a fresh solution 10 converge in each new cycle in the peritoneum 2 of the patient 1 during the inflow of fresh dialysis solution 10. The residual solution 20 is formed by residual fluid of the preceding cycle and is composed of the previously administered dialyzate fluid and ultrafiltration fluid. The mass transport properties of the residual solution 20 differ from those of the fresh solution 10. Looked at in isolation, it is even conceivable that the residual solution 20 provides a resorption. The question arises as to how fast the two solutions 10 and 20 mix with one another in the abdomen and what properties this mixed solution has. During the inflow, a portion of the fresh dialyzate solution 10 mixes with the residual solution 20 due to the inward flow. The subsequently beginning diffusion has the effect that a concentration balance of the two solutions 10 and 20 has taken place at a time x. A homogeneous mixed solution 30 will presumably be present in the peritoneum 2 after a relatively short time period, as shown in FIG. 4.

Figure 5:
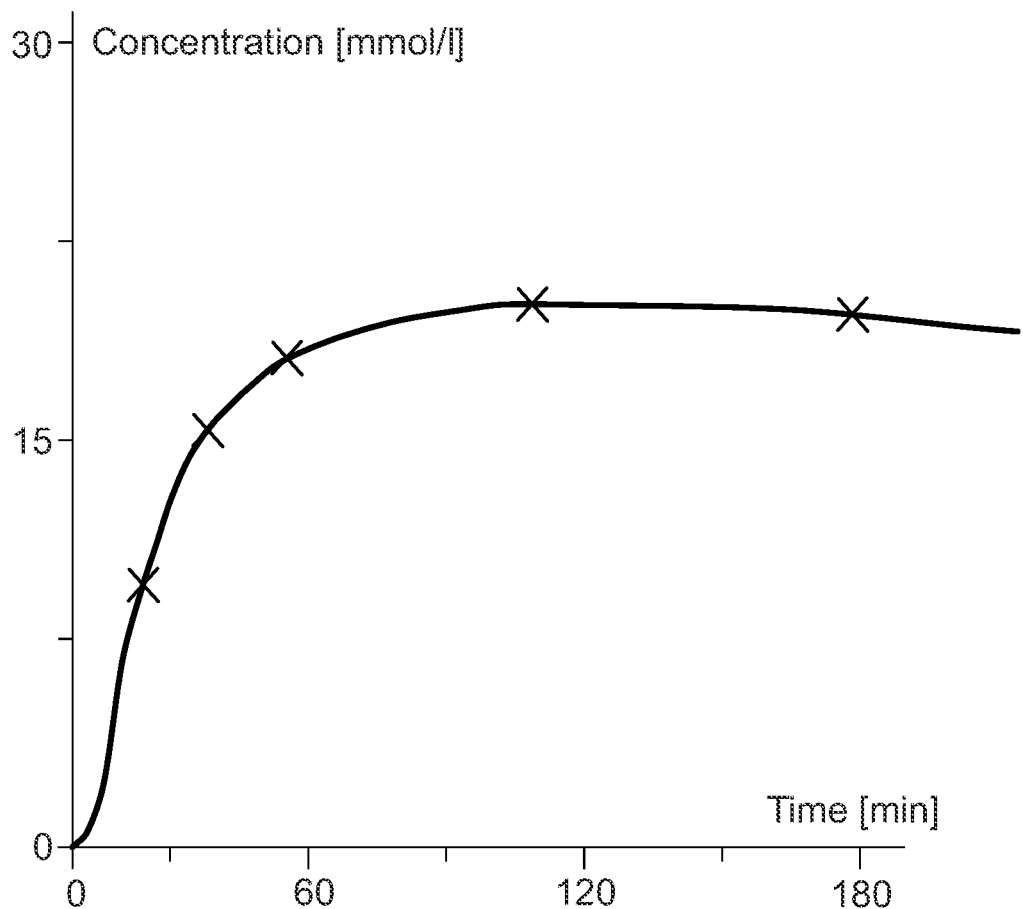
FIG. 5: a schematic representation of a resorption curve for a solute replaced during a peritoneal dialysis treatment.
Figure 6:
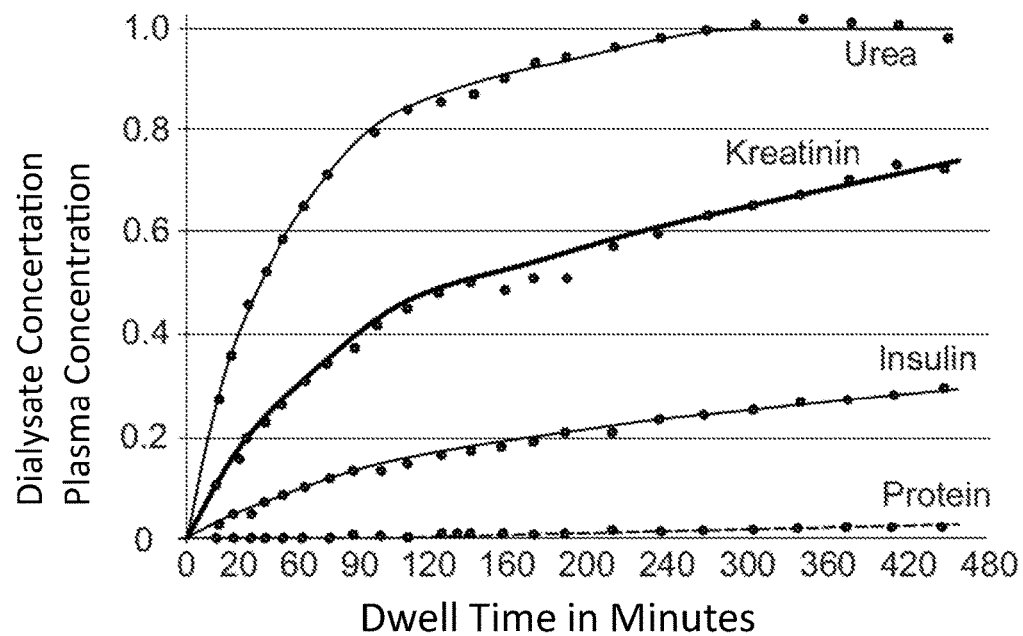
FIG. 6: different resorption curves for different solutes.

A resorption curve such as shown by way of example in FIG. 5 provides a statement on the effectiveness of the detoxification during the dwell phase. The time progression of the resorption curve depends on whether the patient is a high transporter or a low transporter. A high transport capacity here means that a concentration equalization of the dissolved particles quickly takes place between the blood and the dialyzate, in accordance with a steep curve progression at the start and a fast reaching of a steady state. The steepness of the resorption curve further depends on the glucose concentration or on the kind of solution used. As can be seen from FIG. 6, different substances have different resorption curves. They are generally flat and approximately linear for large molecules such as proteins and insulin.

It is common to all the resorption curves for smaller molecules that the concentration gradient has a relatively high and linear progression at the start of the dwell phase. This means that the effective mass transport remains constant in the initial time. The dependence of the mass transport on the administered inflow volume is not shown in FIG. 6. It is rather assumed in the representations that the patient has been ideally filled with fresh solution. In reality, however, the properties of the residual solution 20 and its amount would also have to be taken into account. It must at least be assumed that there is a deterioration of the mass transport properties with respect to the idealized observations of FIG. 6 due to the influence of the residual solution.

Provision is now made in accordance with the present invention to use inflow volume that is not needed in order to replace small portions of the begun solution of the peritoneum during the dwell phase to achieve an additional mass transport. This concept is visualized in FIG. 7, with the y axis showing the filling volume in the peritoneum of the patient. Within the framework of the example shown, the permitted residual volume is fixed at 1000 ml (lower horizontal line) and the permitted patient volume is fixed at 3400 ml (upper horizontal line). The prescription is shown by the theoretical (lower) treatment curve and does not take account of any residual volume. Within the framework of the actual treatment in accordance with the higher treatment curve, dialysis fluid actually planned in accordance with the prescription always remains when the prescribed inflow volume together with the residual volume still present in the peritoneum before the start of the respective inflow phase would result in a total volume that exceeds the permitted patient volume. In the example shown, a respective additional partial replacement takes place during the dwell phase in cycles 4, 6, and 8, with the unused and thus excess inflow solution being consumed in so doing. This is symbolized by the serrated lines. No partial replacement takes place in the odd cycles because the dwell times are smaller in relation so that the use of the available excess volume in these cycles would be less effective. No residual volume is yet available in cycle 2.

Within the framework of the invention, the partial replacement should always take place during a dwell phase. Preferred times for the start of a partial replacement start after the elapse of approximately half the dwell time and end on the elapse of approximately 80% of the dwell time since in the normal case the dialyzate is no longer as effective at this time as at the start of the treatment and, on the other hand, the refreshed solution can still sufficiently develop its effect.

Figure 8:
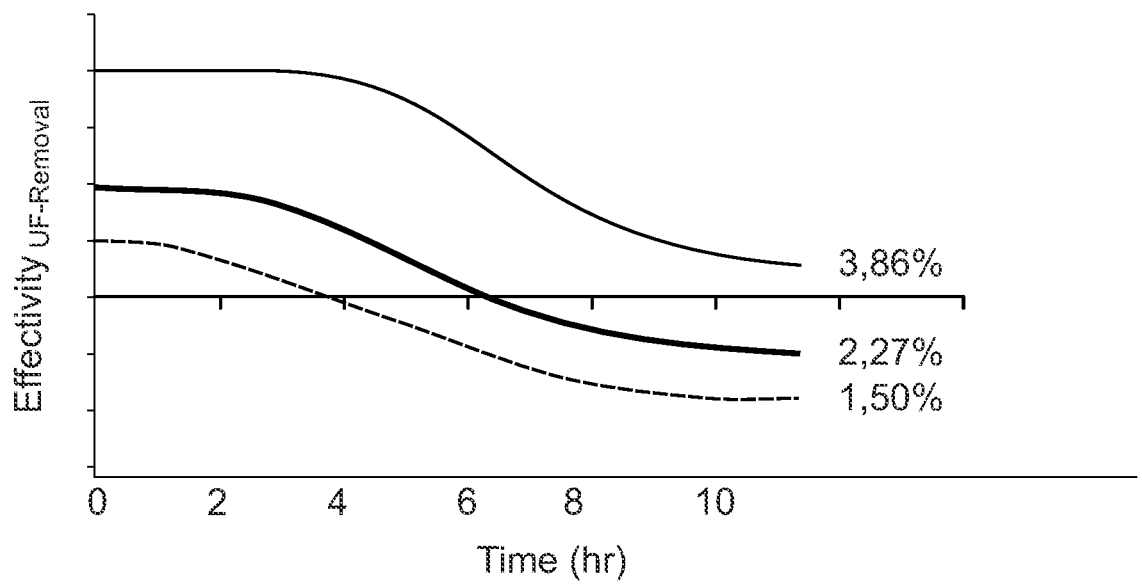
FIG. 8: a representation showing the effectiveness of the UF generation for solutions having glucose concentrations of 3.86%, 2.27%, and 1.50%.

In an example, the prescribed inflow volume can amount to 3000 ml and the residual volume can be fixed at 50%, that is, 1500 ml. The maximum volume is set at 110%, that is, 3300 ml. If a new inflow phase is started directly on a reaching of the residual volume, a maximum of only 1800 ml may therefore flow into the patient. The percentage portion of the residual solution thus amounts to (1500/3300)*100%=45%. Since the effectiveness of dialysis solutions drops with the dwell time in the peritoneum, as can be seen from the relationship shown in FIG. 8, this can have significant effects on the treatment efficiency.

Figure 9:
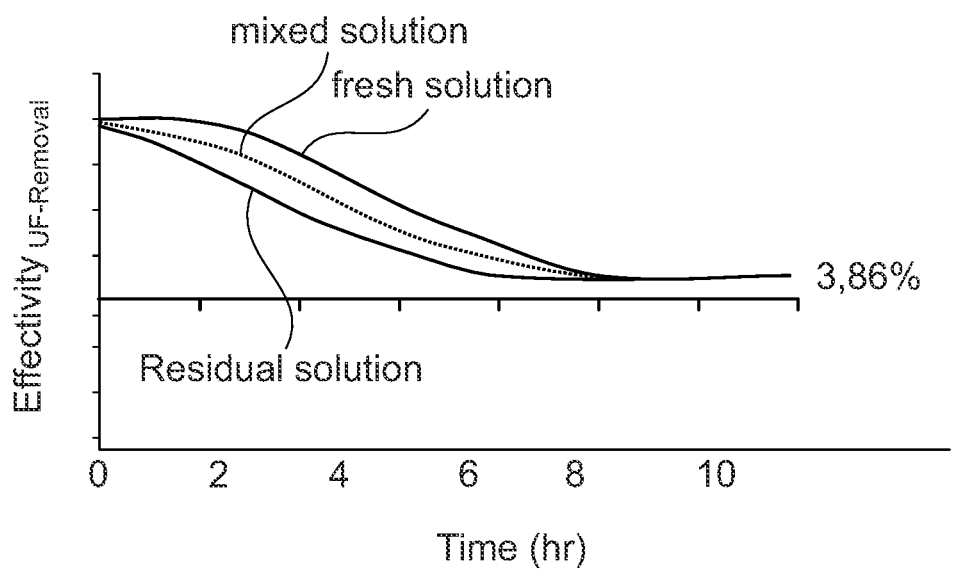
FIG. 9: illustration of the effectiveness of a mixed solution of fresh and consumed dialysis solution.

Under the assumption that the residual fluid is only composed of dialyzate (no UF portion) that has on average been present in the abdomen for approximately 2 h, an effectiveness of the mixed solution results for the constellation named in the example that is between the effectiveness of fresh dialysis solution in total and the 45/55 mixture. This is illustrated graphically in FIG. 9 where the effectiveness of the removal for UV volumes (=UF effectiveness) is shown for the fresh solution. The UF effectiveness of the residual solution results from the UF effectiveness curve of the fresh solution shifted to the left by 2 hours. The effectiveness of the mixed solution results through an additive superposition while using the assumption that the mix relationship amounts to approximately 50% as in the above sample calculation. In reality, the residual solution will still contain ultrafiltration volume that has an effectiveness of zero. It is therefore achieved by the partial replacement of the solution in accordance with the invention that the blood-dialyzate concentration gradient is increased and the effectiveness of the treatment thus increases.

Figure 7:
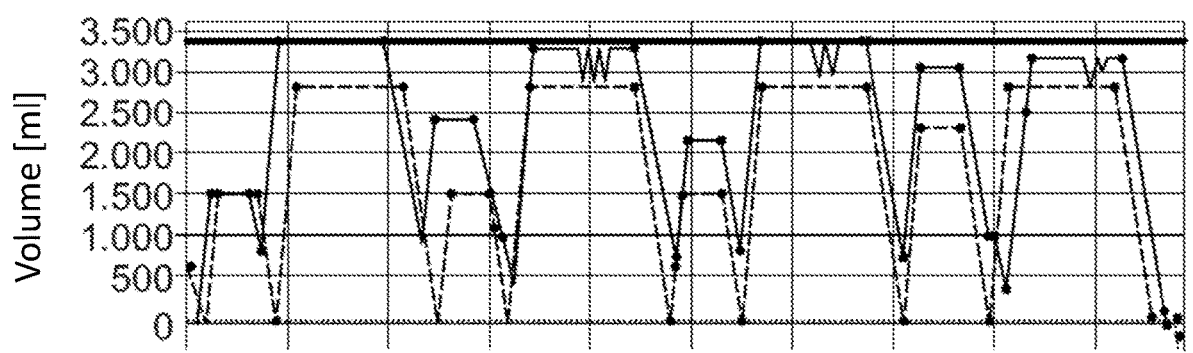
FIG. 7: a filling volume time diagram for a process management in a peritoneal dialysis treatment using a device in accordance with the invention.
Figure 10:
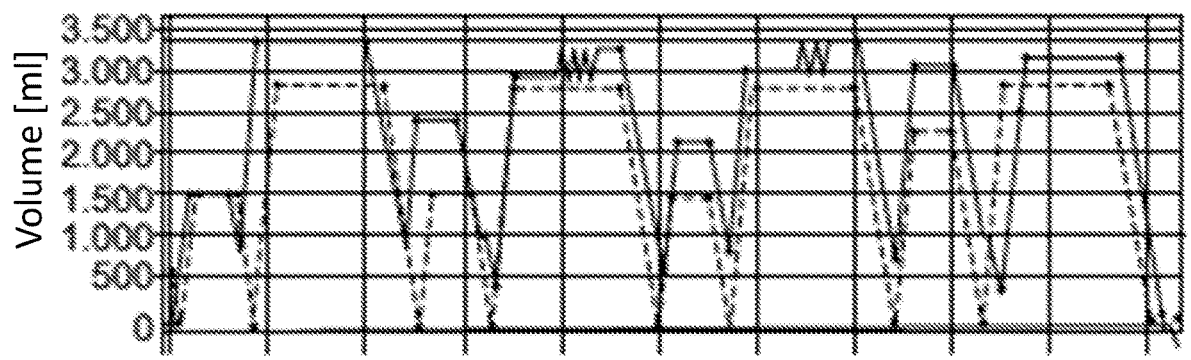
FIG. 10: a filling volume time diagram for an alternative process management in a peritoneal dialysis treatment using a device in accordance with the invention.

An alternative to the routine likewise in accordance with the invention shown in FIG. 7 is shown in FIG. 10. The partial replacement cycles there start with an inflow to generally avoid outflow pressure problems. The volume of the previous inflow phase can be reduced by the volume of the inflow for the partial replacement cycle in this variant, as has been shown in the Figure.

The partial replacement is distributed over a plurality of cycles in both the embodiment of FIG. 7 and in the embodiment of FIG. 10. This has efficiency reasons, on the one hand; on the other hand, the situation with respect to the existing residual volume can, however, also change in the course of the treatment. Dialysis solution thus may have to be discarded, for example, if problems occur or if pumps are repositioned.

Figure 11:
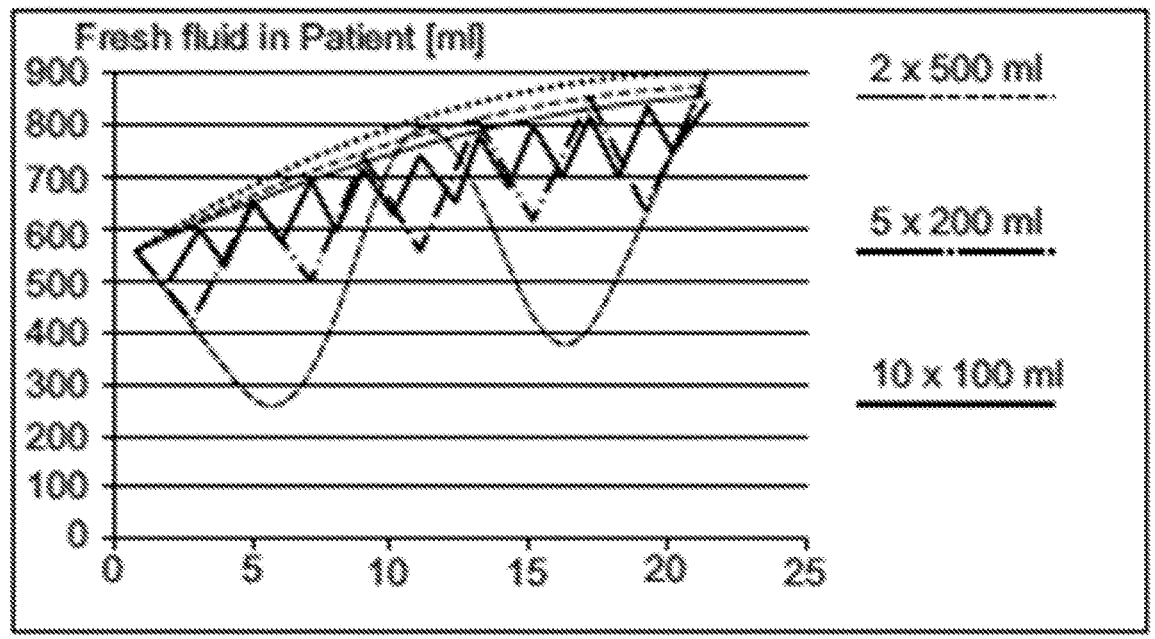
FIG. 11: an exemplary representation of portions of the partial replacement volume in the peritoneum.

It can be meaningful within the framework of the invention to design the effective partial replacement volume during the partial replacement process to be as high as possible. The proportion of the fresh solution in the peritoneum is shown in FIG. 11, while using the above sample calculation, in dependence on the number and volume of the partial replacement cycles. Once the regular inflow had been administered, 550 ml fresh solution and 450 ml residual solution were present in the abdomen of the patient. The higher the replacement volumes, the higher the proportion of fresh solution at the end, as can be seen from the following Table 1 that reflects the values of the diagram of FIG. 11.

TABLE 1

| Partial replacement cycles | Fresh solution in the abdomen beforehand | Fresh solution in the abdomen afterward |
| --- | --- | --- |
| 10 × 100 ml | 550 ml | 843 ml |
| 5 × 200 ml | 550 ml | 852 ml |
| 2 × 500 ml | 550 ml | 887 ml |

Figure 12:
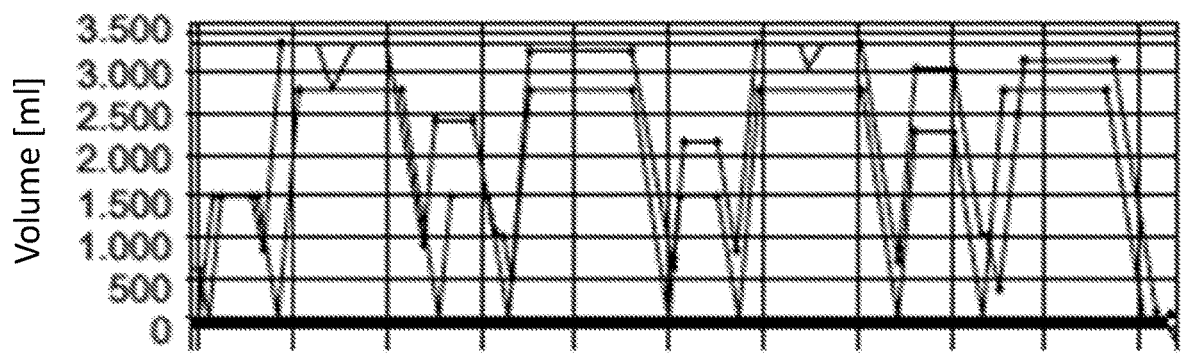
FIG. 12: a filling volume time diagram for a further process management in a peritoneal dialysis treatment using a device in accordance with the invention.

A further embodiment of the invention is shown in FIG. 12. Partial replacement processes are only carried out as part of two cycles in this embodiment. It may not make any sense to generate a partial replacement cycle for cycles having short dwell times due to the short residence time.

Figure 13:
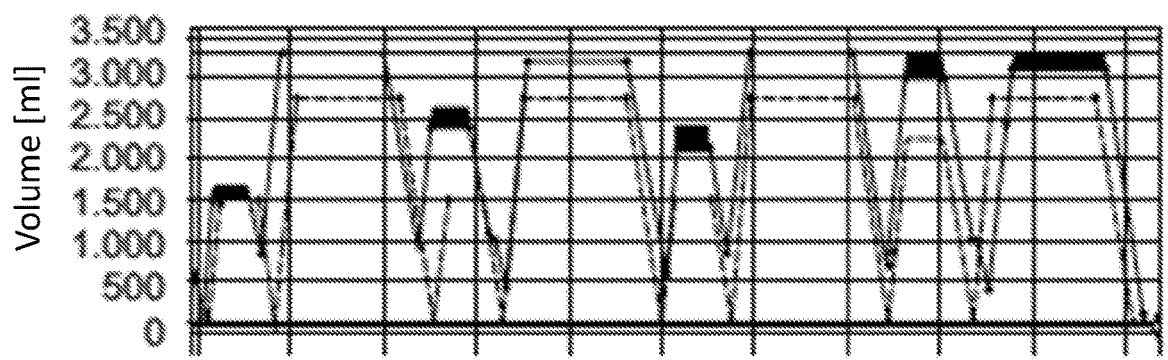
FIG. 13: a filling volume time diagram for yet another process management in a peritoneal dialysis treatment using a device in accordance with the invention.

Provision is made in variant of the concept in accordance with the invention that unused inflow solution is alternatively or additionally used to slightly increase inflows, as can be seen from the representation in FIG. 13. The maximum permitted patient volume may naturally not be exceeded here. This variant of the process management could be advantageous for adapted prescriptions since cycles having small and large inflow volumes alternate in this treatment form. The cycles with the small inflow volumes could be raised within predefined limits of, for example, 10%.

Advantages of the concept in accordance with the invention comprise hardly any or at least less fluid being conducted to the drainage. The total connected solution volume can be sensibly consumed for the treatment. Time-intensive and know-how intensive workarounds such as the preparation of tidal prescriptions or subsequent editing are no longer required. The disadvantages of the workarounds are compensated. The adaptation takes place very dynamically and in dependence on the situation. The efficiency of the treatment is increased. The patient cannot be overfilled. No time delays for treatments are required. No additional disturbances are to be expected so that the patient does not have to be woken up due to the process management. The concept works with profiled treatments.

Figure 14:
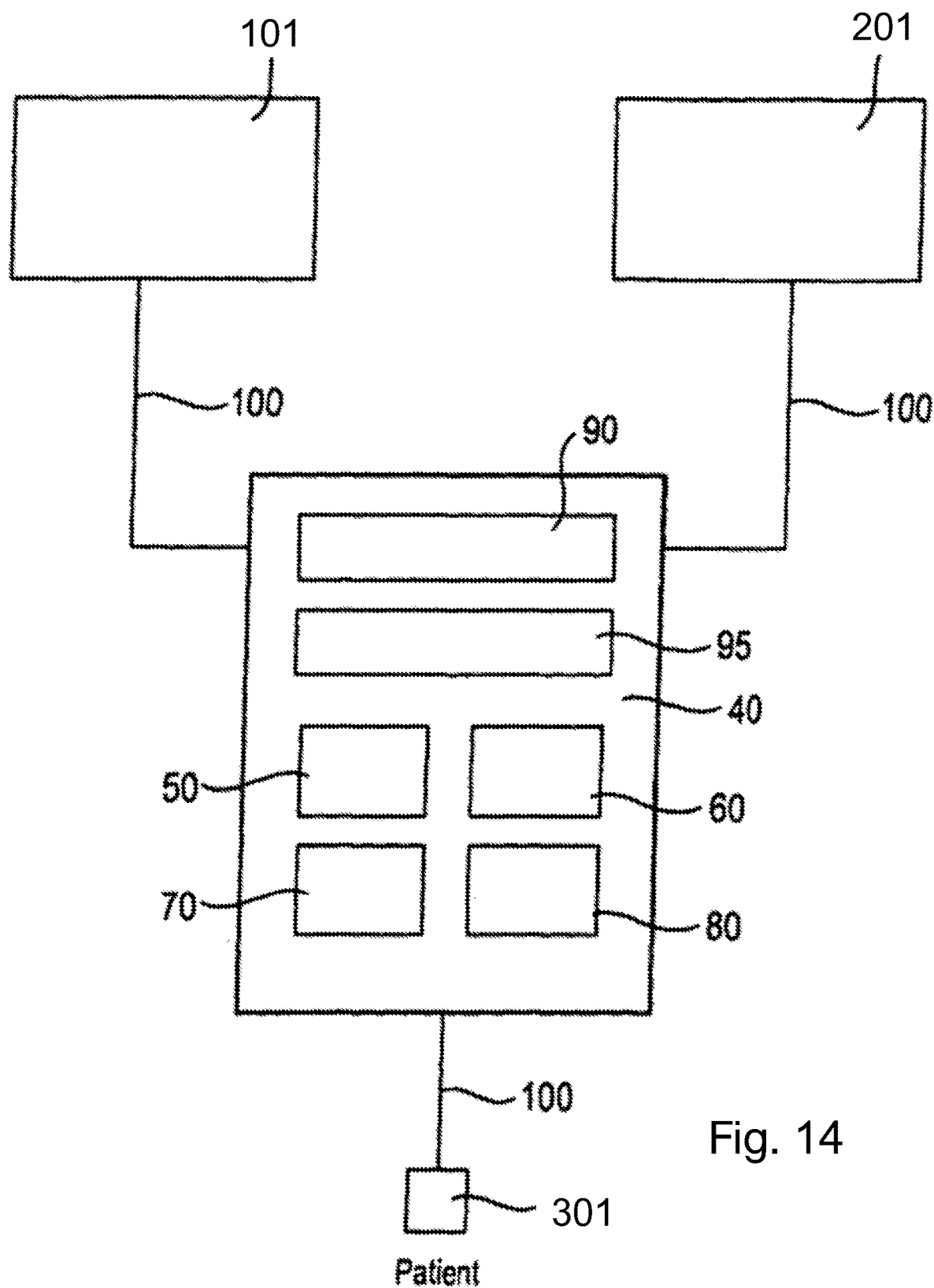
FIG. 14: a schematic diagram of a peritoneal dialysis system.

The construction of an exemplary peritoneal dialysis system is shown schematically in FIG. 14. The peritoneal dialysis system comprises a container 101 with fresh dialysate, and a drain 201 for used dialysate. Furthermore, a connector 301 is provided and can be connected to a catheter of a patient in order to either introduce fresh dialysate into the abdominal cavity of the patient or to remove used dialysate from the abdominal cavity. Container 101 with fresh dialysate, drain 201 for used dialysate, and connector 301 to the patient, are connected to one another via fluid paths 100 and together with these form the fluid system of the peritoneal dialysis system.

A dialysis machine 40 is provided for carrying out a peritoneal dialysis treatment. Dialysis machine 40 comprises a pump 50 that conveys fresh dialysate from container 101 to the connector 301, and transports spent dialysate from the connector 301 to the drain 201. Valves 70 are provided to control the flows of liquids. Valves 70 open and close fluid paths 100 so as to establish corresponding fluid connections between container 101, connector 301, and drain 201. A heater 60 can be provided. Sensors 80 monitor and control a proper sequence of treatment.

The components of dialysis machine 40 are controlled via a controller 90. Controller 90 controls pump 50, heater 60, and valves 70 on the basis of data received from sensors 80. The controller 90 controls the sequence of peritoneal dialysis. Controller 90 can control and/or include a balancer 95 that balances the quantities of liquid added and removed from the patient.

The invention claimed is:

1. An apparatus for carrying out a peritoneal dialysis treatment comprising a reservoir for fresh dialysis fluid, a connector for connecting to a peritoneal catheter of a patient, a drain for consumed dialysis fluid, and a control unit connected to actuators, wherein the apparatus is configured to:

carry out a plurality of consecutive inflow-dwell-outflow cycles for a treatment on a basis of a prescription stored in the control unit, in which inflow-dwell-outflow cycles dialysis fluid is supplied to the patient from the reservoir and is led off of the patient through an outflow after a dwell time in the peritoneum of the patient, each inflow-dwell-outflow cycle being provided, in accordance with the prescription, with a respective dwell time and a respective volume of fresh dialysis fluid;

determine that the respective volume of fresh dialysis fluid of at least one of the inflow-dwell-outflow cycles was not completely consumed during the at least one inflow-dwell-outflow cycle; and during one or more subsequent inflow-dwell-outflow cycles, subsequent to the at least one inflow-dwell-outflow cycle, conduct a premature partial replacement whereby a portion of the dialysis fluid present in the peritoneum of the patient is replaced, with fresh dialysis fluid from the reservoir, before the elapse of the respective dwell time for the one or more subsequent inflow-dwell-outflow cycle, whereby the premature partial replacement is carried out based on the determination that the respective volume of fresh dialysis fluid provided, in accordance with the prescription, for the at least one inflow-dwell-outflow cycle was not completely consumed during the at least one inflow-dwell-outflow cycle.

2. The apparatus in accordance with claim 1, wherein a volume of dialysis fluid present in the peritoneum is replaced as part of the premature partial replacement, and the volume of dialysis fluid that is replaced is a maximum of 50% of the total volume of dialysis fluid present in the peritoneum.

3. The apparatus in accordance with claim 2, wherein the dwell time of the one or more subsequent inflow-dwell-outflow cycle is not extended or reduced by the premature partial replacement; and/or in that the total volume of dialysis fluid present in the peritoneum of the patient is not changed by the premature partial replacement.

4. The apparatus in accordance with claim 2, wherein the premature partial replacement is carried out in a plurality of inflow and removal steps and/or with a maximum of 200 ml being supplied with each inflow step.

5. The apparatus in accordance with claim 2, wherein the premature partial replacement is only carried out after the elapse of at least 50% of the respective dwell time for the one or more subsequent inflow-dwell-outflow cycle, and the premature partial replacement is ended before the elapse of a maximum of 80% of the respective dwell time for the one or more subsequent inflow-dwell-outflow cycle.

6. The apparatus in accordance with claim 2, wherein the apparatus is configured to supply the patient with the total volume of dialysis fluid provided in accordance with the prescription in the course of the treatment, with any difference quantity that is not supplied as part of the regular inflow phases being completely supplied as part of the premature replacement during the at least one or more inflow-dwell-outflow cycles.

7. The apparatus in accordance with claim 2, wherein the premature partial replacement is carried out in a plurality of inflow and removal steps directly consecutive.

8. The apparatus in accordance with claim 2, wherein the premature partial replacement is carried out in a plurality of inflow and removal steps with at least five inflow steps being provided.

9. The apparatus in accordance with claim 2, wherein the apparatus is configured to supply the patient with the total volume of dialysis fluid provided in accordance with the prescription in the course of the treatment, with any difference quantity that is not supplied as part of the regular inflow phases being completely supplied on a basis of a consideration of the maximum volume, as part of the premature replacement during the at least one or more inflow-dwell-outflow cycles.

10. The apparatus in accordance with claim 1, wherein the apparatus is configured to already replace a portion of the dialysis fluid present in the peritoneum of the patient in a plurality of the inflow-dwell-outflow cycles over the course of the treatment, with fresh dialysis fluid from the reservoir, before the elapse of the respective dwell times of the plurality of inflow-dwell-outflow cycles.

11. The apparatus in accordance with claim 1, wherein the apparatus is configured only to start a premature partial replacement during a respective one of the inflow-dwell-outflow cycles when the dwell Mien time provided for the respective cycle, in accordance with the prescription, exceeds a minimum time.

12. The apparatus in accordance with claim 1, wherein a maximum volume of dialysis fluid that may be present in the peritoneum of the patient is fixed in the control unit and that the incomplete consumption of the volume of fresh dialysis solution provided for the at least one inflow-dwell-outflow cycle results from the fact that the complete consumption would have led to an exceeding of the maximum volume.

13. The apparatus in accordance with claim 1, wherein a volume of dialysis fluid present in the peritoneum is replaced as part of the premature partial replacement, and the volume of dialysis fluid replaced is a maximum of 30% of the total volume of dialysis fluid present in the peritoneum.

14. The apparatus in accordance with claim 1, wherein a volume of dialysis fluid present in the peritoneum is replaced as part of the premature partial replacement and the volume of dialysis fluid that is replaced is a maximum of 20% of the total volume of dialysis fluid present in the peritoneum.

15. An apparatus for carrying out a peritoneal dialysis treatment comprising a reservoir for fresh dialysis fluid, a connector for connecting to a peritoneal catheter of a patient, a drain for consumed dialysis fluid, and a control unit connected to actuators, wherein the apparatus is configured to:

carry out a plurality of consecutive cycles for one treatment on the basis of a prescription stored in the control unit, in which inflow-dwell-outflow cycles dialysis fluid is supplied to the patient from the reservoir and is led off through the drain again after a dwell time elapses in the peritoneum of the patient, each of the inflow-dwell-outflow cycles being provided with a respective dwell time and a respective volume of fresh dialysis fluid, in accordance with the prescription;

determine that the respective volume of fresh dialysis fluid of at least one of the inflow-dwell-outflow cycles was not completely consumed during the at least one inflow-dwell-outflow cycle; and increase a total inflow volume in at least one of the inflow-dwell-outflow cycles subsequent to the at least one inflow-dwell-outflow cycle, based on the determination that the respective volume of fresh dialysis fluid provided in accordance with the prescription for the at least one inflow-dwell-outflow cycle was not completely consumed during the at least one inflow-dwell-outflow cycle.

16. The apparatus of claim 15, wherein the apparatus is further configured to already replace a portion of the dialysis fluid present in the peritoneum of the patient with fresh dialysis fluid from the reservoir before the elapse of the respective dwell time of the at least one inflow-dwell-outflow cycle if, in at least one inflow-dwell-outflow cycle, the volume of fresh dialysis fluid provided in accordance with the prescription for the at least one inflow-dwell-outflow cycle was not completely consumed.

* * * * *